(12) United States Patent
Alshaer

(10) Patent No.: US 12,208,197 B2
(45) Date of Patent: Jan. 28, 2025

(54) MANUALLY OPERATED NEGATIVE PRESSURE WOUND TREATMENT APPARATUS COUPLED WITH SMART FEEDBACK SYSTEM

(71) Applicant: Hisham Alshaer, Mississauga (CA)

(72) Inventor: Hisham Alshaer, Mississauga (CA)

( * ) Notice: Subject to any disclaimer, the term of this patent is extended or adjusted under 35 U.S.C. 154(b) by 0 days.

(21) Appl. No.: 17/543,760

(22) Filed: Dec. 7, 2021

(65) Prior Publication Data

US 2022/0184295 A1  Jun. 16, 2022

Related U.S. Application Data

(60) Provisional application No. 63/124,104, filed on Dec. 11, 2020.

(51) Int. Cl.
*A61M 1/00* (2006.01)

(52) U.S. Cl.
CPC ............ *A61M 1/962* (2021.05); *A61M 1/684* (2021.05); *A61M 1/912* (2021.05); *A61M 1/966* (2021.05); *A61M 2205/073* (2013.01); *A61M 2205/18* (2013.01); *A61M 2205/3324* (2013.01); *A61M 2205/3327* (2013.01); *A61M 2205/3553* (2013.01); *A61M 2205/50* (2013.01); *A61M 2205/581* (2013.01); *A61M 2205/584* (2013.01); *A61M 2205/8206* (2013.01)

(58) Field of Classification Search
CPC ...... A61M 1/962; A61M 1/684; A61M 1/912; A61M 1/966; A61M 2205/073; A61M 2205/18; A61M 2205/3324; A61M 2205/3327; A61M 2205/3553; A61M 2205/50; A61M 2205/581; A61M 2205/584; A61M 2205/8206; A61M 1/95; A61M 1/982; A61M 2205/07; A61M 2205/075; A61M 1/81; A61M 1/815; A61M 1/90; A61M 1/96; A61M 1/98; A61M 1/984; A61M 1/985
See application file for complete search history.

(56) References Cited

U.S. PATENT DOCUMENTS 3,742,952 A * 7/1973 Magers ................. A61M 1/684
　　　　　　　　　　　　　　　　　　　　 604/133
3,938,514 A * 2/1976 Boucher ............. A61M 3/0262
　　　　　　　　　　　　　　　　　　　　 222/206

(Continued)

*Primary Examiner* — Susan S Su
*Assistant Examiner* — Ted Yang
(74) *Attorney, Agent, or Firm* — Kevin J Fournier Intellectual Property Legal Services Ltd.; Kevin J Fournier

(57) ABSTRACT

A negative pressure wound treatment (NPWT) apparatus for suction of bodily fluids using the negative pressure generated by means of manual pressing. The NPWT apparatus is made of two parts: [1] top functional part; and [2] bottom collector part. The top functional part is made of a pressing mechanism attached to a bellow enclosed within an enclosure which creates negative pressure sucking the bodily fluid from the wound. The bottom collector part is attached with the bellow through the internal one-way valve, wherein the collector collects the fluid from the bellow. Pressure levels and wound conditions are measured and transmitted to the user's smart device, in order to enhance treatment monitoring and efficacy.

1 Claim, 7 Drawing Sheets

(56) References Cited

U.S. PATENT DOCUMENTS

| | | | | |
|---|---|---|---|---|
| 4,141,361 A * | 2/1979 | Snyder | A61M 1/684 | 604/133 |
| 4,278,089 A * | 7/1981 | Huck | A61M 1/684 | 417/328 |
| 4,392,860 A * | 7/1983 | Huck | A61M 1/684 | 604/212 |
| 4,460,354 A * | 7/1984 | Weilbacher | A61M 1/684 | 604/181 |
| 4,529,402 A * | 7/1985 | Weilbacher | A61M 1/684 | D24/111 |
| 4,578,060 A * | 3/1986 | Huck | A61M 1/68 | 604/134 |
| 4,709,705 A * | 12/1987 | Truglio | A61M 3/0262 | 604/38 |
| 5,019,059 A * | 5/1991 | Goldberg | A61M 1/684 | 604/317 |
| 5,102,404 A * | 4/1992 | Goldberg | A61M 1/684 | D24/117 |
| 5,279,550 A * | 1/1994 | Habib | A61M 1/81 | 604/38 |
| 5,628,305 A * | 5/1997 | Melker | A61M 16/0075 | 128/205.15 |
| 5,678,564 A * | 10/1997 | Lawrence | A61F 5/455 | 600/573 |
| 6,174,306 B1 * | 1/2001 | Fleischmann | A61B 17/085 | 604/543 |
| 6,261,276 B1 * | 7/2001 | Reitsma | A61M 1/67 | 604/319 |
| 6,840,923 B1 * | 1/2005 | Lapcevic | A61F 5/442 | 604/319 |
| 2005/0002810 A1 * | 1/2005 | Gould | F04B 45/02 | 417/472 |
| 2007/0010798 A1 * | 1/2007 | Stoller | A61M 1/81 | 604/320 |
| 2008/0108977 A1 * | 5/2008 | Heaton | A61M 1/78 | 604/355 |
| 2008/0200905 A1 * | 8/2008 | Heaton | A61M 1/784 | 604/543 |
| 2009/0234260 A1 * | 9/2009 | Coward | A61M 27/00 | 601/148 |
| 2009/0254066 A1 * | 10/2009 | Heaton | A61M 1/784 | 604/543 |
| 2010/0030166 A1 * | 2/2010 | Tout | A61M 1/684 | 604/316 |
| 2010/0262094 A1 * | 10/2010 | Walton | A61M 1/81 | 604/319 |
| 2010/0305490 A1 * | 12/2010 | Coulthard | A61F 13/022 | 604/313 |
| 2012/0071845 A1 * | 3/2012 | Hu | A61M 1/985 | 604/319 |
| 2012/0209225 A1 * | 8/2012 | Hu | A61M 1/98 | 604/319 |
| 2013/0023719 A1 * | 1/2013 | Bennett | A61B 5/0002 | 601/149 |
| 2013/0144227 A1 * | 6/2013 | Locke | A61M 1/743 | 604/319 |
| 2014/0163489 A1 * | 6/2014 | Walti | A61M 1/784 | 422/292 |
| 2015/0018784 A1 * | 1/2015 | Coulthard | A61M 1/92 | 604/319 |
| 2015/0088033 A1 * | 3/2015 | Locke | A61M 39/223 | 600/573 |
| 2016/0184497 A1 * | 6/2016 | Phillips | G16H 20/10 | 604/319 |
| 2018/0169308 A1 * | 6/2018 | Hu | A61M 1/60 | |
| 2019/0030221 A1 * | 1/2019 | Locke | A61M 1/604 | |
| 2019/0054218 A1 * | 2/2019 | Locke | A61M 1/74 | |
| 2019/0298899 A1 * | 10/2019 | Hu | A61M 1/80 | |
| 2020/0368408 A1 * | 11/2020 | Coulthard | A61M 1/96 | |

* cited by examiner

# MANUALLY OPERATED NEGATIVE PRESSURE WOUND TREATMENT APPARATUS COUPLED WITH SMART FEEDBACK SYSTEM

CROSS REFERENCE TO RELATED APPLICATION

This application claims the benefit of U.S. Provisional Application No. 63/124,104 filed on Dec. 11, 2020, by the present inventor; the disclosure is hereby incorporated herein by reference.

FIELD OF INVENTION

The present invention relates to a wound treatment device. More particularly, it is a manually operated negative pressure wound treatment apparatus that generates negative pressure in a self-confined area by means of manual pressing.

BACKGROUND OF INVENTION

Open wounds result from acute injuries, such as traffic accidents or building collapse, or chronic injuries such as bed sores or diabetic foot. These wounds take several weeks to months to close using the conventional gauze therapy. In the process, pus and bacteria collect in the wound causing infections, which puts the risk of the patient at septicemia, amputation, or even death.

Negative pressure wound therapy (NPWT) is a proven method to treat open wounds which accelerates healing dramatically which is achieved by applying continuous negative pressure on the wound at level between −80 to −120 mmHg. The negative pressure during these treatments, acts by drawing blood supply into the wound pad, removing excess fluid and bacteria, and mechanically shrinking the wound size.

Thus, it would be desirable to have a device that may produce adequate negative pressure, yet effective, low cost, and portable. Further, it is desirable to have a non-electric device that can be used in absence of electrical power to serve patients in such localities. Moreover, there is a need of a device that combines efficiency, effectiveness, safety, low cost, mobility, and independence from electrical power.

SUMMARY

This summary is provided to introduce a selection of concepts in a simplified form that is further disclosed in the detailed description of the invention. This summary is not intended to identify key or essential inventive concepts of the claimed subject matter, nor is it intended for determining the scope of the claimed subject matter.

The present invention provides a simple yet effective, manually operated apparatus for negative pressure wound treatment. According to one embodiment, it is a self-contained, manually operated apparatus that generates negative pressure by means of manual pressing. The apparatus of present invention is consists of: a piston attached with a bellow and enclosed within an enclosure such that when the bellow is not compressed, the piston head levels above the enclosure. The apparatus further includes an aperture at the side of the enclosure to allow an external medical tube to connect with the bellow through an external one-way check valve, wherein the external medical tube connects the bellow with the wound while the one-way check valve prevents fluid to flow in the direction from bellow towards the wound.

According to one embodiment, the apparatus further comprises a canister affixed at the bottom of the enclosure and connected with the bellow through an internal one-way check valve. When the user manually presses the piston, it compresses bellow causing the fluid and air present within the bellow to enter within the canister through the internal one-way check valve that prevents the fluid to flow back into the bellow from canister. The bellow has a passive spring expansion property. Then, as the compression of the bellow is released, the expansion force creates negative pressure (suction) within it as well as on wound which is directly connected with the bellow using the external medical tube. The generated negative pressure causes the bodily fluid from the wound to exude and enter within the bellow. With gradual collection of bodily fluid within the bellow causes gradual loss of negative pressure within the bellow that in-turn causes bellow to expand and hence the piston to move upward. When the negative pressure within the bellow reaches to zero, the bellow expands completely causing the piston head to level completely above the enclosure.

According to one embodiment, various visual indicators are affixed over the piston head to visually display the pressure level within the bellow manually and to alert the user when to press the piston again. As long as the wound is air-sealed, the patient needs to press the devices only once to generate the negative pressure. The apparatus of present invention is fully functional without electrical power or any external electrical connection, which makes it very mobile and ergonomic.

According to one embodiment, the present invention is superior to electrical. NPWT methods because (1) it produces negative pressure between −80 to −120 mmHg without the need for electrical power, which makes it conducing to resource constrained environments such as refugee camps, (2) It is very ergonomic which makes it very easy to apply by doctors and nurses with minimal failure rate, and (3) It can be used by the patient with minimal instructions in the home due to its ergonomic design and the visual indicator of the negative pressure.

Further, the invention is superior to other manual NPTW devices because it is furnished with an integrated canister that is connected to the main body as a single unit, which the patient can detach and clean without disrupting the treatment. This allows utility with bloody or wet wounds that release a lot of secretions. The level of fluids collected in the canister can be visually monitored by the patient. The degree of negative pressure can be visually observed by the patient as a manifestation of the piston height above the enclosure, which can be further enhanced by color strips (e.g., green or red) to correlate with negative pressure; a process that does not require any electrical power.

According to one embodiment, the NPWT device of the present invention offers few variations for manual pressing, either by vertical pressing on the device, or hand pressing on a soft bladder extending from the device, which enhances the ergonomics from user patient perspective. The NPWT device can be furnished with an electronic module for monitoring performance and wound condition for physician and patient feedback. According to one embodiment, the present invention can have bladder instead of piston to manually press the apparatus. The apparatus also contains an electronic circuit board which contains microprocessor, buzzer and LED light indicator to send alerts to the user when the negative pressure decreases to the level below the therapeutic range, coin battery to provide power to all the devices on the circuit, PH sensor to detect early signs of wound infection and Bluetooth module as a communication module to communicate between the NPWT apparatus and the user device.

BRIEF DESCRIPTION OF DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and structures disclosed herein. The description of a method step or a structure referenced by a numeral in a drawing is applicable to the description of that method step or structure shown by that same numeral in any subsequent drawing herein.

DETAILED DESCRIPTION OF INVENTION

Figure 1:
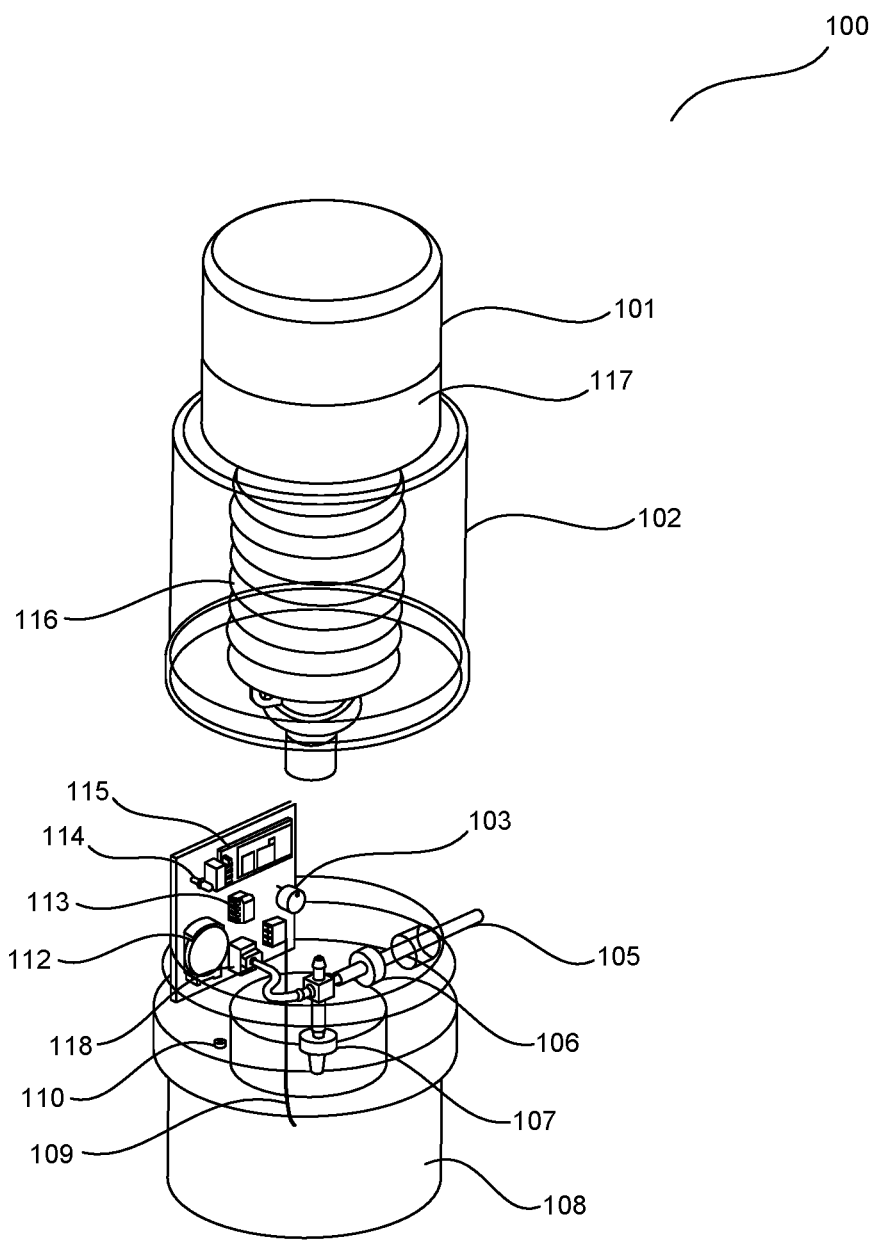
FIG. 1 shows exploded view of manually operated negative pressure wound treatment apparatus having an electronic circuit board to be inserted in the hollow part of the top enclosure in the device and an external medical tube connected to the bellow through an internal inward one-way check valve above the canister.

The present invention overcomes the aforesaid drawbacks of the above, and other objects, features and advantages of the present invention will now be described in greater detail. Also, the following description includes various specific details and are to be regarded as merely exemplary. Accordingly, those of ordinary skill in the art will recognize that: without departing from the scope and spirit of the present disclosure and its various embodiments there may be any number of changes and modifications described herein.

According to one embodiment, a fully manually operated negative pressure wound treatment apparatus provided by the present invention that can function without the electronic module, making it more compact, economical and effective solution for treating wounds using the negative pressure. The manually operated negative pressure wound treatment apparatus of present invention is made of two main parts including [1] an upper functional part (top enclosure) and [2] lower fluid container part (canister).

The upper functional part is made of a piston attached with a bellow enclosed within the enclosure and creates a negative pressure within the enclosed portion when the bellow is manually compressed using a piston. The lower part is a canister attached at the bottom of the upper functional part to collect the bodily fluid coming out of the wound during treatment According to one embodiment, the canister is a normal food container with a twist top, wherein the lid of the twist top container is fixed at the bottom of the enclosure that allows the container to removably attach with the lid during treatment. According to an embodiment, the piston and bellow assembly is enclosed within the enclosure in a way that the piston head is levelled above the enclosure when the bellow are in full relaxed and in an expanded position that provides a visual indication about the negative pressure within the enclosure. According to an embodiment, the bellow is made of plastic. According to one another embodiment, the bellow is made of rubber or PVC or coated nylon or coated fiberglass or metals. According to one embodiment, all the parts are made of off-the-shelf components already used in medical and food industry and therefore, suitable for medical devices.

According to one embodiment, the enclosure includes an opening at the side for connection of an external tube that connects the apparatus with the wound. The external tube connects the enclosure through an internal one-way check valve that allows the bodily fluid to flow from the wound side to the enclosure side only. According to one embodiment, the enclosure further includes an aperture at the bottom centre of the enclosure that opens in canister which also includes a one-way check valve as an internal valve that allows movement of bodily fluid from the bellow to the canister underneath. According to one embodiment, the enclosure base above the canister contains a vent which helps the air to flow out from the apparatus while the apparatus is in use.

Referring to FIG. 1 now which shows exploded view of the embodiment of present manually operated negative pressure wound treatment (NPWT) apparatus 100, hereafter referred as NPWT apparatus 100. According to the present embodiment, the NPWT apparatus 100 is made of an upper functional part that creates a negative pressure for treatment, when pressed manually. The upper functional part is comprised of enclosure 102 enclosing all the functional parts of the NPWT apparatus 100. A piston 101 is attached with the bellow 116 and enclosed within the enclosure 102 such that the upper head of the piston 101 levels above the enclosure when it is not pressed and the bellow 116 are in normal extracted condition.

According to present embodiment, the upper functional part further includes aperture at the bottom of the enclosure wherein the side aperture is configured to connect the external medical tube 105 that further connects the apparatus 100 with the wound dressing, while the bottom aperture 107 is configured for bodily fluid to collect within the collector or canister 108 from the bellow 116. The NPWT apparatus 100 of the present embodiment further includes one-way check valves 106 and 107 at both the apertures to allow fluid to flow only in one direction, from the wound to bellow 116 and from bellow to the canister 108. According to the present embodiment, the bottom part of the NPWT apparatus 100 is a twist top container that works as a canister 108 to collect the bodily fluid coming from the wound. The top lid of the container is fixed at the bottom of the enclosure 102 such that the container can easily be removed from the lid for cleaning, by just twisting the container.

While using the present NPWT apparatus 100, the wound is first covered with special plastic plaster to make it an air-sealed compartment and external medical tube 105 is connected through the wound pad. The external medical tube 105 is then connected with the bellow 116 of the apparatus 100 through a one-way check valve 106. At the beginning of the treatment, when the piston 101 is pressed manually, the bellow 116 connected with the piston 101 is compressed which pushes the existing fluid (if any from a previous treatment) from the bellow 116 into the canister 108 through the internal one-way check valve 107. The bellow 116 then starts to expand spontaneously, by means of its spring properties, which creates a negative pressure/vacuum within the bellow 116. This in-turn pulls fluids from the wound through the external tube and creates a negative pressure at the wound pad e.g., −100 mmHg. As fluid flows from the wound, the bellow 116 gets filled gradually decreasing the negative pressure to zero, fully expanding the bellow 116. Expansion of the bellow 116 pushes the piston 101 upward above the level of the enclosure 102 which offers a visual indication to the user that the piston needs to be pushed again in order to re-establish the negative pressure within the bellow 116. In next cycle, when the piston 101 is again pushed manually, it compresses the bellow 116 which in-turn pushes the collected fluid into the canister 108 through the internal one-way check valve 107 while the external one-way check valve 106 prevents the fluid from flowing towards the wound again.

According to the present embodiment, a colour scale 117 is affixed at the levelled-up head portion of the piston that visually indicates the level of the piston 101 and hence the present negative pressure level within the bellow 116. According to one embodiment, straps of various colour shades may be affixed at various levels over the head portion of the piston 101, i.e., green at the top, red at the bottom and various other colour shades in between making only green colour to be visible when piston 101 is pressed, and other colours to become gradually visible with gradual de-compression/pressure loss within the bellow. According to one exemplary embodiment, all the pressure levels indicating colour straps automatically become visible when bellow are fully expanded and the piston 101 levels above the enclosure 102, due to zero negative pressure. According to one embodiment, the indication may be shown using a numerical scale of pressure level. According to one embodiment, instead of using different straps of colours, one single visual analog scale, single colour scale, colour coded numerical scale etc.

According to one embodiment, the canister 108 is used also as a base of the apparatus 100 making the device less prone to breakage and detachment compared to the ones having a separate bottle or a container attached to the side of the enclosure. According to one embodiment, the canister 108 is a conventional twist top food container making the device more economical and also suitable for medical use.

According to one another embodiment, the NPWT apparatus 100 of the present invention may include an electronic unit embedded inside the pump enclosure communicatively coupled with a pressure transducer 118 which is connected within the cavity of the bellow 116 via a hollow tube. The electronic unit includes electronic controller, communication module, and sensors communicatively and physically coupled with the mechanical components of the apparatus. The electronic unit may allow the user to monitor the level of negative pressure accurately over the smart device of the user such as a smartphone or any other smart device. According to one embodiment, the apparatus may include a pressure detection sensor 118 mounted within the apparatus to detect a real time pressure level within the bellow 116 and canister 108. The communication module 115 (e.g., Bluetooth or Wi-Fi) of the present invention transmits the reading of the sensor to the connected smart user devices to allow the user to monitor it. According to one more embodiment, the electronic controller of the system 113 collects the real time data from the pressure sensor, compares it with the lower threshold value of pressure, and visually as well as audibly alerts the user, if the pressure level within the bellow 116 drops below the threshold value.

According to one more embodiment, the system may include a buzzer 103 communicatively coupled with the electronic controller that may alert the user when the pressure level decrease from the threshold value so that the user may re-press the piston 101 to create a negative pressure within the bellow 116.

According to one more embodiment, the electronic unit further includes microprocessor 113, wherein the pressure detection sensor measures the negative pressure of the bellow 116 and conveys the reading to the microprocessor, which digitizes the readings using an analog-to-digital converter. The electric circuit further includes a communication module 115 communicatively coupled with the controller to communicate the reading with an external portable smart device such as smartphone, tablet, or any other wearable smart device. According to one embodiment, the communication module is a Bluetooth module 115. According to one embodiment, the electric unit may transmit the pressure reading intermittently e.g., every few seconds or minutes depending on the need in order to maintain low power consumption. According to one embodiment, the electric unit contains coin battery 112 to provide long lasting, reliable power to various devices connected on the circuit board.

According to one embodiment, the system for treatment of wound using manually operated negative pressure treatment apparatus may further include a computer software or a mobile application at a receiver side capable of being accessed using any smart device, where the software or the mobile application is designed to connect with the control unit of the electric circuit to receive the pressure reading from the control unit. The software or the mobile application is configured to provide visual feedback through LED light indicator 114 located on the circuit board to auditory feedback through buzzer 103 situated on the board or alert the user when the negative pressure decreases to the level below the therapeutic range i.e., the therapeutic pressure range is −80 to −100 mmHg.

According to one embodiment, the software or mobile application can be put on a sleep mode when there is no need of therapy or when the user/patient goes to sleep. According to one embodiment, the control software may include AI (artificial intelligence) powered algorithms to detect any severe leakage or rupture within the dressing and inform the patient to visit the caregiver to resolve the issue. According to one embodiment, the software or mobile application may store the pressure data points in order to extrapolate a trend of treatment such as total time of negative pressure vs. no negative pressure, frequency of manual activation, the degree of leakage based on long term analysis of said data.

According to one more embodiment, the system may directly send the data to the treating physician to inform significant issues such as major leakage that requires frequent manual activation or non-compliance of the patient based on which the physician may intervene remotely by communicating with the patient and correct an unwanted situation.

According to one embodiment, the wound treatment apparatus of the present system may further detect early signs of wound infection using wound acidity. Research shows that the healthy wound normally has a low pH (from 4-5) while the increase in pH (from 6 to 10) indicates wound infection and poor healing. According to one embodiment, the apparatus includes a pH measuring probe 109 inserted within the canister 108, where fluid is collected. The pH measuring probe 109 is further connected with the control unit of the electrical circuit board to transfer the pH readings to the control unit which digitizes said readings and transmits them to the connected smart device for the user or the physician to monitor over the software or mobile application. Further, the AI algorithm of the software or mobile application analyses said pH data and estimates the degree of infection, defines the probability of future health of wound from said readings, and also allows early intervention, such as administering of antibiotics to prevent serious consequences such as hospitalization or amputation. According to one embodiment, the electronic controller is also configured to transmit any information generated by the device and through use of the device which includes but is not limited to the frequency of piston presses, the duration the device is used, the time the device was disconnected, the average pressure level, the duration of the treatment and other information along with its timestamp.

According to one embodiment, the enclosure base situated at the bottom side of the top enclosure 102 contains a hole 110 for ventilation that lets the air pass through the apparatus when in use. When the piston 101 is pressed manually, the bellow 116 connected with the piston 101 also compresses which pushes the existing fluid from the bellow 116 into the canister 108 through the internal one-way check valve 107. The bellow 116 then starts to expand spontaneously, by means of its spring properties, which creates a negative pressure/vacuum within the bellow 116. This inturn pulls fluids from the wound through the external tube and creates a negative pressure at the wound. As fluid flows from the wound, the bellow 116 gets filled gradually decreasing the negative pressure to zero and simultaneously throws the air out of the hole 110 for further use.

Figure 2:
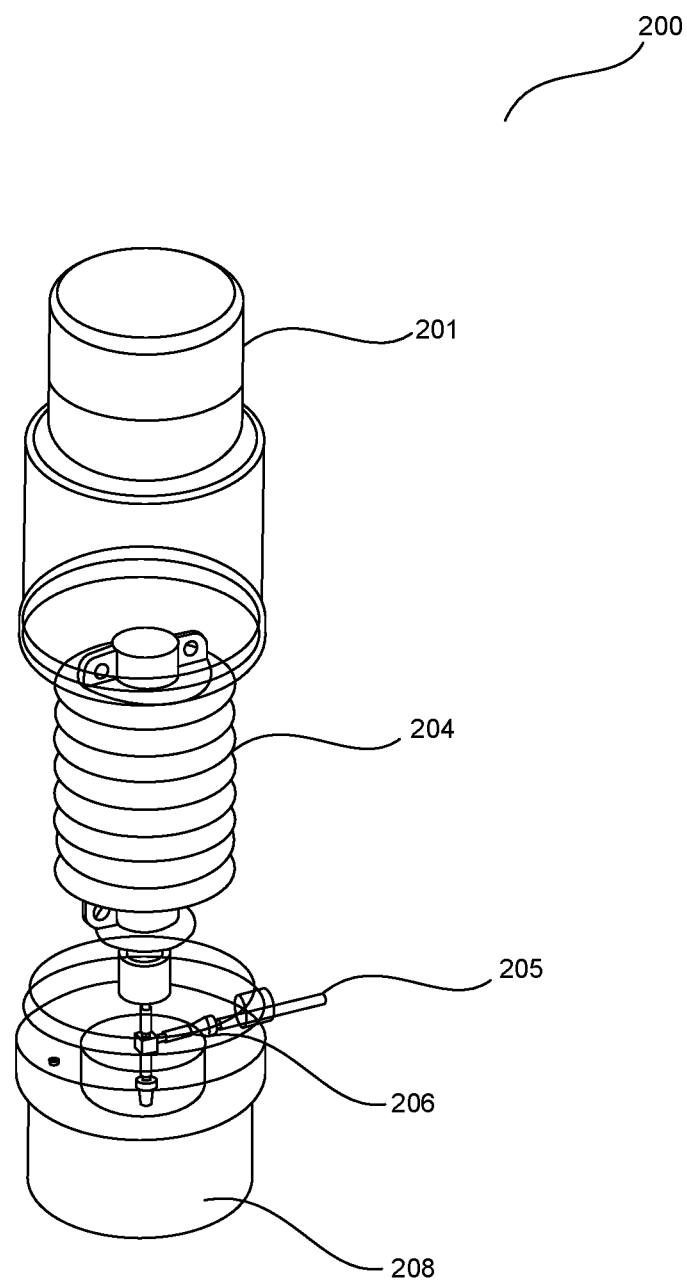
FIG. 2 shows exploded view of manually operated negative pressure wound treatment apparatus without the circuit board in the device, describing another embodiment of the invention.

FIG. 2 shows another exploded view of the embodiment of manually operated negative pressure wound treatment apparatus 200 without the circuit board in the device. According to this embodiment, the piston 201 of the NPWT apparatus 200 when pressed manually compresses the bellow 204. The bellow will then expand spontaneously due to its spring properties causing negative pressure/vacuum to create within the bellow. This negative pressure/vacuum draws fluid from the wound into the bellow 204 through the external medical tube 205. One end of the external medical tube 205 is connected with the bellow 204 through internal one-way check valve 206 and the other end of the external medical tube 205 is connected to the wound dressing. Due to the subsequent compression of the bellow 204, the fluid collected in the bellow 204, flows in one direction towards the canister 208. The one-way check valve 206 prevents back flow of fluid towards the wound making it easier for the user to collect the fluid in the canister.

Figure 3:
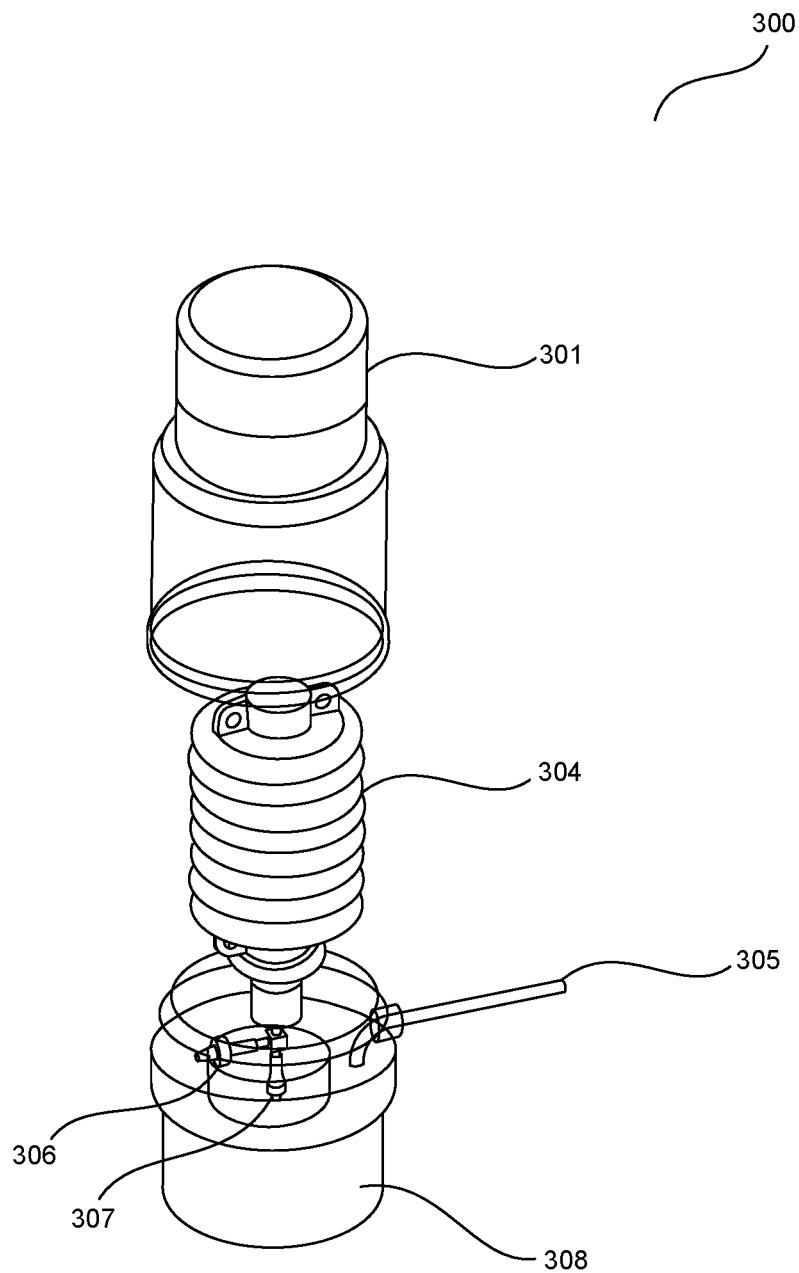
FIG. 3 shows exploded view of manually operated negative pressure wound treatment apparatus having an external medical tube directly connected to the canister through an internal one-way check valve showing one more embodiment of the invention.

FIG. 3 shows exploded view of the embodiment of the manually operated negative pressure wound treatment apparatus 300 having an external medical tube 305 connected directly with canister 308. According to the present embodiment, the NPWT apparatus 300 includes an external medical tube 305 connected directly with canister 308 instead of bellow 304, while the direction of the internal one-way check valves 307 is also inverted. According to the present embodiment, the piston 301 of the NPWT apparatus 300 when pressed manually compresses the bellow 304 causing air to flow through one-way check valve 306 to the outside. As the bellow expands spontaneously with its own spring properties, negative pressure/vacuum is created within the bellow 304 and thus within the canister 308 since it is directly connected with the bellow 304 through an internal one-way check valve 307, which is rotated and now allows only flow of air from the bellow 304 to the canister 308. The external medical tube 305 is connected with the canister 308 connecting the wound with the canister 308. While using this embodiment, the negative pressure present within the canister 308 created by the bellow 304 causes bodily fluid to enter directly within the canister 308 through the external medical tube 305 thus keeping the components of the upper functional part free from liquid. Since the body fluids get collected directly within the canister 308, it makes it easier for the user to clean the apparatus as the canister 308 is a twist-top container.

Figure 4:
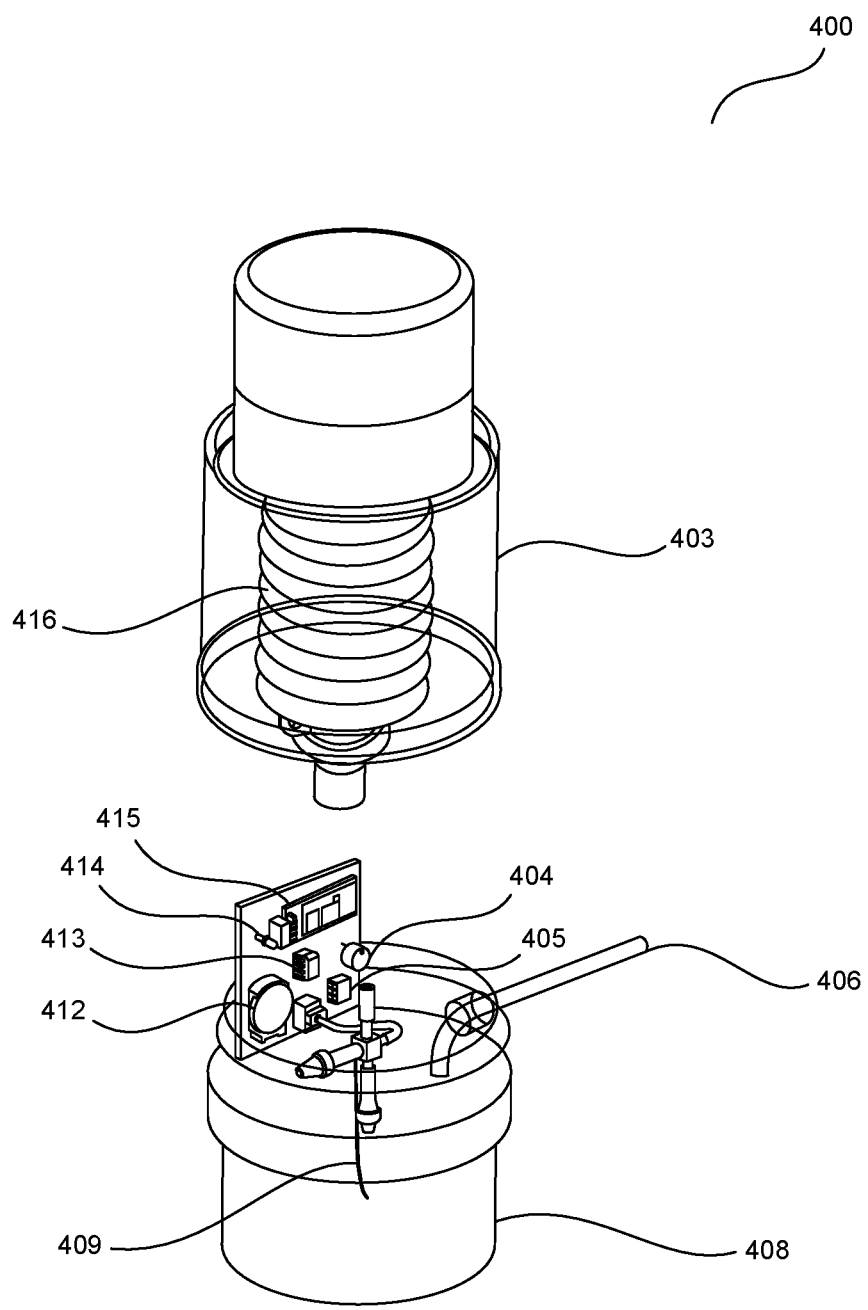
FIG. 4 shows exploded view of the manually operated negative pressure wound treatment apparatus having an electronic circuit board placed in the hollow part of the top enclosure in the device with external medical tube connected directly to the canister through an internal one-way check valve.

FIG. 4 shows another exploded view of the embodiment of the manually operated negative pressure wound treatment apparatus 400 having an electronic circuit board situated in the hollow part of the top enclosure 403. One end of the external medical tube 406 is connected directly with the canister 408, while the other end of the external medical tube is connected with the wound. The electronic circuit board contains an electronic controller, communication module, and sensors communicatively, and physically coupled with the mechanical components of the apparatus. The circuit board includes microprocessor 413, buzzer 404 and LED light indicator 414 to send alerts to the user when the negative pressure decreases to the level below the therapeutic range, coin battery 412 to provide power to all the components on the circuit, PH sensor 405 to detect early signs of wound infection through a pH probe 409, and Bluetooth module 415 as a communication module to communicate between the NPWT apparatus and the user device. While using this embodiment, the negative pressure present within the canister 408 created by the bellow 416 causes bodily fluid to enter directly within the canister 408 through the external medical tube 406 instead of going passing through the bellow and upper part of the apparatus, thus, keeping the components of upper functional part free from liquid and making it easy to use the apparatus.

Figure 5:
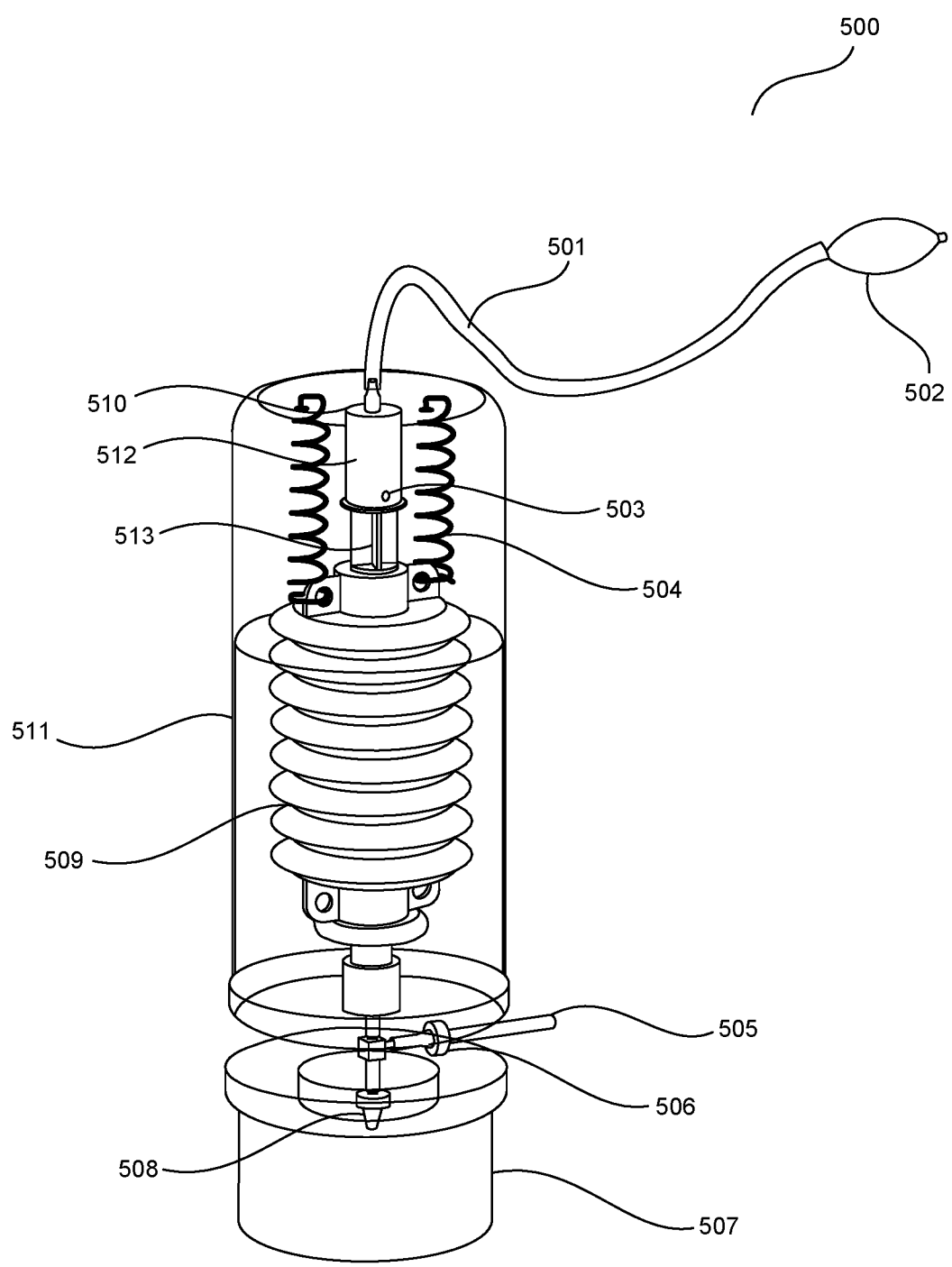
FIG. 5 shows front view of the manually operated negative pressure wound treatment apparatus having a soft rubber bladder to manually press the apparatus and internal springs connecting the bellow to the top enclosure, wherein the bellow is enclosed within the top enclosure.

FIG. 5 shows another exploded view of the embodiment of manually operated negative pressure wound treatment apparatus 500 having a spring connected between the enclosure top wall and the bellow 509. According to one embodiment, the NPWT apparatus comprises a soft rubber bladder 502 instead of a piston and a tube 501 connected to the bladder 502. The soft rubber bladder 502 and the tube 501 can be connected to a linear expansion mechanism. According to one embodiment, the linear expansion mechanism is syringe 512 within the enclosure 511 that is coupled with the tube from any side (e.g., top or side) via a syringe nozzle. According to the present embodiment, the soft rubber bladder 502 is connected to the top surface of the enclosure from outside via a tube 501. One end of the tube 501 is connected to the rubber bladder 502 while the other end is connected to the nozzle of syringe 510 which can protrude outside the enclosure 511. The syringe 512 is connected to pneumatic plunger 513 that helps in creating required pressure through soft rubber bladder 502 towards the bellow 509. The syringe and plunger act as a pneumatic piston, such that air pressure is converted into a linear displacement. It should be noted that this mechanism can be replaced by any other mechanism that serves to convert the fluid pressure, such as air pressure generated by the rubber bladder, to linear motion. According to one embodiment, the external medical tube 505 is then connected with the bellow 509 of the apparatus 500 through a one-way check valve 506. According to this embodiment, the NPWT apparatus 500 includes a spring 504 between top wall of an enclosure 510 and the bellow 509 to enhance the negative pressure generating mechanism. The spring 504 acts to aid the expansion of the bellow 509 increasing suction force and thus the level of negative pressure within the bellow 509. According to one embodiment, the internal spring 504 is a constant force spring which is configured to maintain a more linear negative pressure as the bellow 509 are expanding due to fluid and air inflow because of the characteristic of constant force spring which maintains the same force regardless of its length. Thus, even when the bellow 509 is near full expansion losing its suction ability, the spring 504 continues exerting its force. The syringe 512 located between the bellow 509 and the enclosure 510 acts as a pneumatic piston.

According to one embodiment, at the beginning of the treatment, when the bladder 502 is pressed manually, the syringe is inflated with air and its plunger is displaced downwards, which compresses the bellow 509 and pushes the fluid into the canister 507 through the internal one-way check valve 508. The bellow 509 then starts to expand spontaneously, by means of spring 504, which creates a negative pressure/vacuum within the bellow 509. According to another embodiment, the compression of the bellow 509 also pulls fluids from the wound through the external tube 505 and creates a negative pressure at the wound. According to another embodiment, the syringe has a vent hole 503. The level of the plunger can be capped at a certain level to avoid extra compression by means of a vent 503 in the barrel of the syringe, such that as the plunger is displaced downwards once it reaches the vent level, the compressed air in the barrel is released and the plunger stops.

Figure 6:
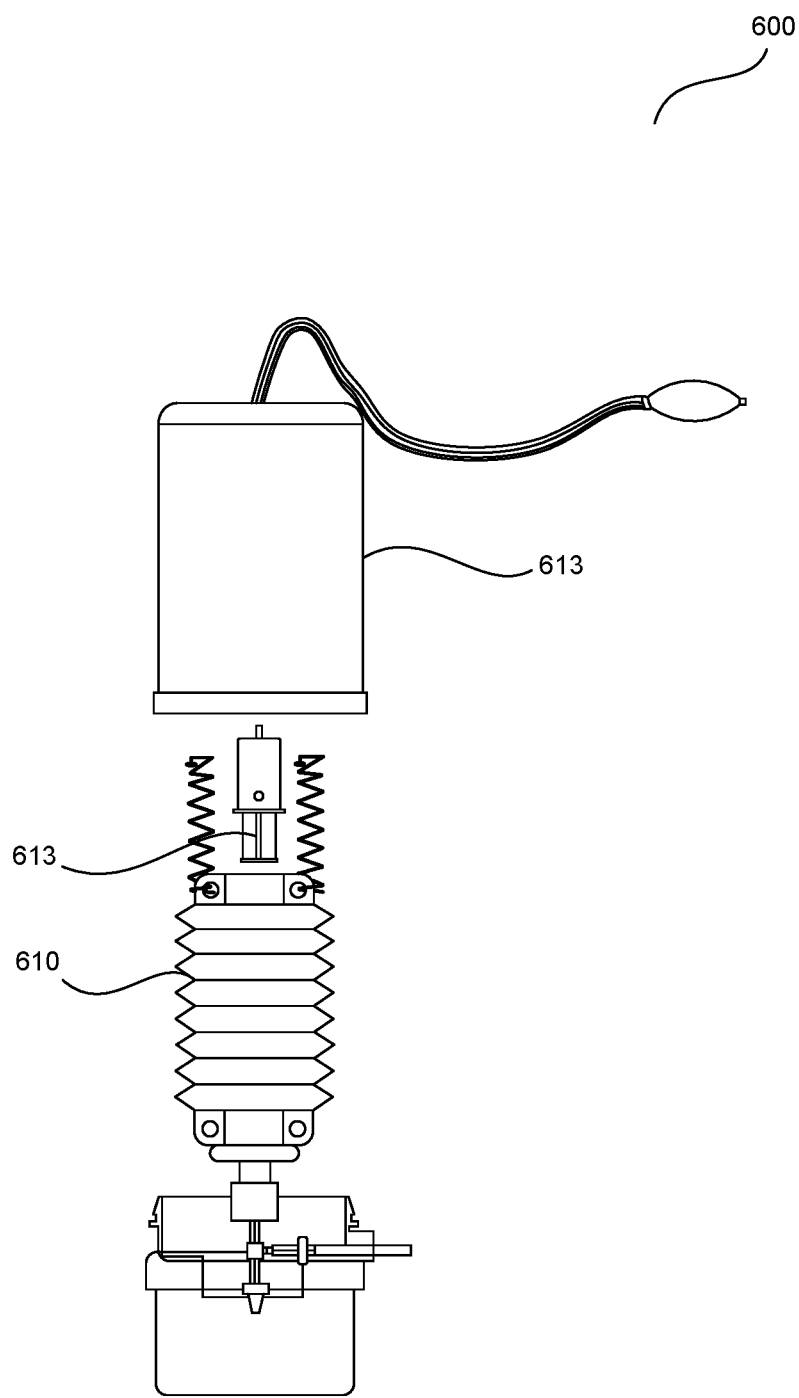
FIG. 6 shows exploded cross sectional view of the manually operated negative pressure wound treatment apparatus having a bladder to manually press the apparatus and internal springs and syringe connected to top enclosure part and bellow.
Figure 7:
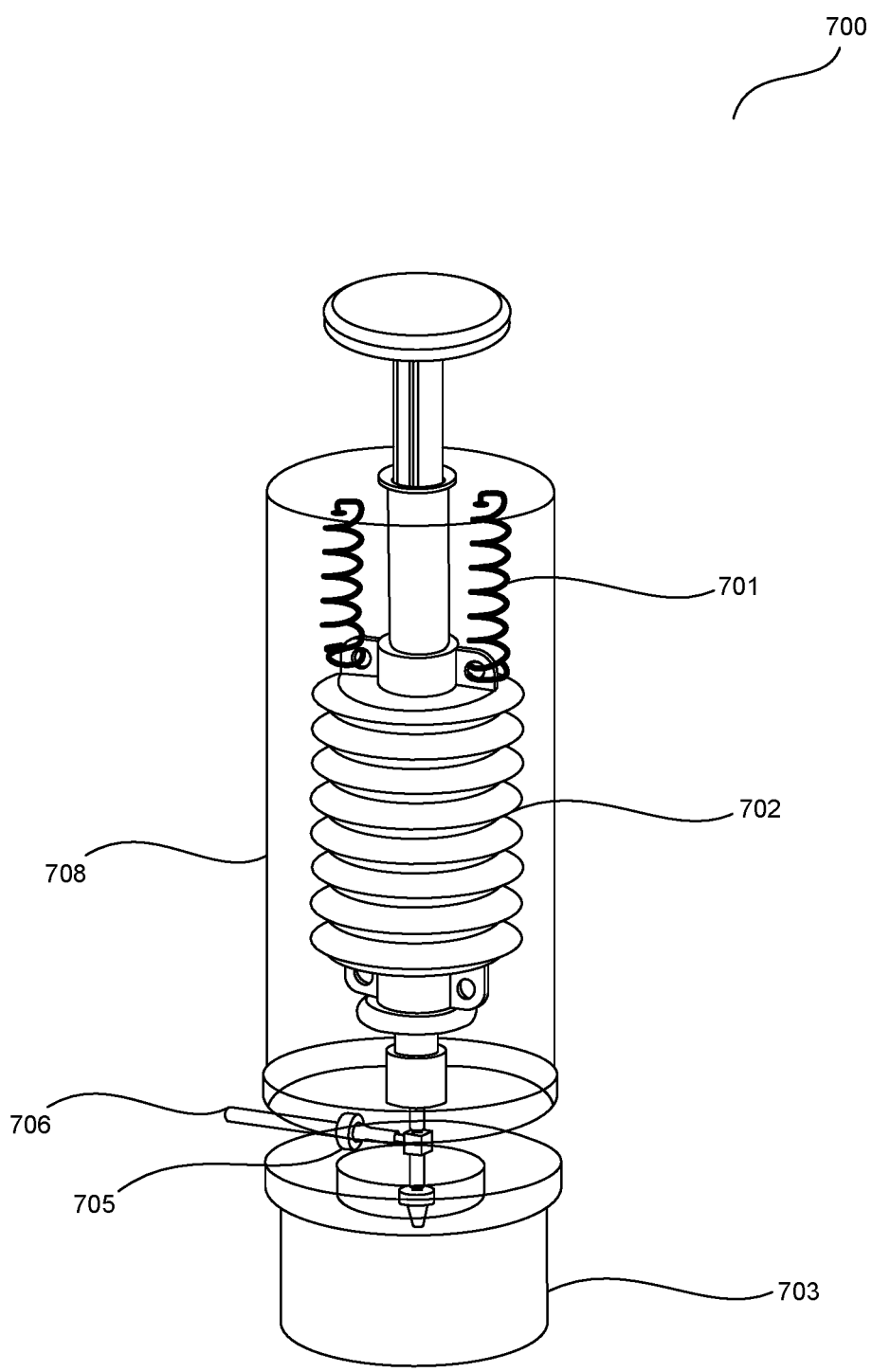
FIG. 7 shows front view of the manually operated negative pressure wound treatment apparatus having internal springs connected with the bellow and top enclosure and external medical tube is connected to the bellow through one way check valve above the canister.

FIG. 6 shows a cross sectional exploded view of the manually operated negative pressure wound treatment apparatus 600 having a spring connected between top enclosure 613 and bellow 610. FIG. 7 shows another exploded embodiment of manually operated negative pressure wound treatment apparatus 700 having a plunger connected to a spring which is connected between the enclosure top wall 708 and the bellow 702. The bellow 702 and other embodiment are enclosed inside the top enclosure 708. One end of the external medical tube 706 is attached with the bellow 702 through an internal one-way valve 705 while the other end of the external medical tube 706 is connected to the wound. When the plunger is pressed manually, it compresses the bellow 702 attached to the piston via springs 701. The springs 701 acts to aid the expansion of the bellow increasing suction force and thus the level of negative pressure within the bellow 702. The internal one-way valve 705 is arranged such that the fluid collected from the wound does not flow towards the wound but flows towards the canister 703. Accordingly, the internal one-way valve between the bellow 702 and canister 703 is arranged in such a manner that allows the remaining fluid in the bellow 702 to flow in the direction of the canister 703.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

The invention claimed is:

1. A negative pressure wound treatment apparatus, comprising:
  an enclosure main body;
  a piston coupled with a bellow via a plurality of springs arranged in parallel and configured within the enclosure main body, wherein a piston head extends out of the enclosure main body in an uncompressed position;
  a strap of colour shades affixed at the levelled-up head portion of the piston to provide visual indication to the user, wherein the strap of colour shades corresponds with negative pressure level within the bellow, becoming gradually visible with gradual de-compression/pressure loss within the bellow; and
  a detachable twist top fluid container affixed at a bottom forming a base of the enclosure main body, wherein the detachable twist top fluid container includes an external medical tube that connects the apparatus to a wound dressing, wherein one end of the external medical tube is connected with the apparatus through an internal one-way check valve.

* * * * *